United States Patent
Brigham-Burke et al.

(10) Patent No.: US 6,346,388 B1
(45) Date of Patent: Feb. 12, 2002

(54) METHOD OF IDENTIFYING AGONIST AND ANTAGONISTS FOR TUMOR NECROSIS RELATED RECEPTORS TR1 AND TR2

(75) Inventors: Michael R. Brigham-Burke, King of Prussia, PA (US); Peter R. Young, Lawrenceville, NJ (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/072,993

(22) Filed: May 6, 1998

Related U.S. Application Data

(60) Provisional application No. 60/055,513, filed on Aug. 13, 1997, provisional application No. 60/056,980, filed on Aug. 26, 1997, and provisional application No. 60/057,550, filed on Aug. 29, 1997.

(51) Int. Cl.[7] .................. G01N 33/53; G01N 33/566; C07K 14/47; C07K 14/705; C07K 17/00
(52) U.S. Cl. ..................... 435/7.1; 435/4; 435/7.2; 435/7.8; 530/350; 530/810; 530/812
(58) Field of Search .................. 435/4, 7.8, 7.1, 435/7.2; 530/350, 810, 812

(56) References Cited

U.S. PATENT DOCUMENTS 5,710,019 A    1/1998    Li et al. .................. 435/69.1

FOREIGN PATENT DOCUMENTS

| EP | 0 308 378 | 3/1989 |
|---|---|---|
| WO | WO9626217 | 8/1996 |
| WO | WO 96/28546 | 9/1996 |
| WO | WO 96/34095 | 10/1996 |
| WO | WO 9701633 | 1/1997 |
| WO | WO 9723614 | 7/1997 |
| WO | WO 9725428 | 7/1997 |
| WO | WO 9733899 | 9/1997 |
| WO | WO 9734911 | 9/1997 |
| WO | WO 9803648 | 1/1998 |
| WO | WO 9818824 | 5/1998 |

OTHER PUBLICATIONS

Ngo et al., in The Protein Folding Problem and Tertiary Structure Prediction, Merz and Le Grand (Eds), Aug. 1994, Springer Verlag, pp. 433 and 492–495.*
Walzak et al., "Trail–R2:a novel apoptosis–mediating receptor for Trail", *J. Embo.*, 16, pp. 5386–5396, 1997.
Simonet et al., "Osteoprotegerin:a novel secreted protein involved in the regulation of bone density", *Cell*, 89, pp. 309–319, 1997.
Kwon et al., "A newly identified member of the tumor necrosis factor receptor etc." *J. Biol. Chem.*, 272, pp. 14272–14276, 1997.
Marsters et al., "Herpes Virus Entry Mediator, a member of the tumor necrosis factor etc.", *J. Biol. Chem.*, 272, pp. 14029–14032, 1997.

Hsu et al., "ATAR, a novel tumor necrosis factor receptor family member, etc.",*J. Biol. Chem.*, 272, pp. 13471–13474, 1997.
Pitti et al., "Induction of apoptosis by Apo–2 ligand, a new member of the tumor etc.", *J. Biol. Chem.*, 271, pp. 12687–12690, 1996.
MacFarlane et al., "Identification and cloning of two novel receptors for the cytotoxic etc.", *J. Biol. Chem.*, 272, pp. 25417–25420, 1997.
Lacey et al., "Osteoprotegerin Lingand is a cytokine that regulates osteoclast etc.", *Cell*, 93, pp. 165–176, 1998.
Mauri et al., "Light, a new member of the TNF superfamily and lymphotoxin etc.", *Immunity*, 8, pp. 21–30, 1998.
Degli–Esposito et al., "Cloning and characterization of Trail–R3 etc.", *J. Exp. Med.*, 186, pp. 1165–1170, 1997.
Yamagucki et al., "Characterization of Structural Domains of Human Osteoclastogenesis etc.",*J. Biol. Chem.*, 273, pp. 5117–5123, 1998.
Pan et al., "The receptor for the cytotoxid ligand Trail", *Science*, 276, pp. 111–113, 1997.
Yasuda et al., "Identity of Osteoclastogenesis inhibitory factor (OCIF) and etc.", *Endocrinology*, 139, pp. 1329–1337, 1998.
Schneider et al., "Trail receptors 1 (DR4) and 2 (DR5) signal FADD–dependent etc.", *Immunity*, 7, pp. 831–836, 1997.
Chaudhary et al., "Death receptor 5, a new member of the TNFR family and DR4 induce etc.", *Immunity*, 7, pp. 821–830, 1997.
Degli–Esposito et al., "The novel receptor Trail–R3 induces NF–kB and protects against etc.",*Immunity*, 7, pp. 813–820, 1997.
Wiley et al., "Identification and characterization of a new member of the TNF etc.", *Immunity*, 3, pp. 673–682, 1995.
Montgomery et al., "Herpes Simplex Virus–1 Entry into cells mediated by a novel member etc.", *Cell*, 87, pp. 427–436, 1996.
Sheridan et al., "Control of Trail–induced apoptosis by a family of signaling and decoy etc.", *Science*, 277, pp. 818–821, 1997.
Pan et al., "An antagonist decoy receptor and a death domain containing etc.", *Science*, 277, pp. 815–818, 1997.
Yasuda et al., "Osteoclast differentiation factor is a ligand for osteoprotegerin etc.", *Proc. Natl. Acd. Sci USA*, 95, pp. 3597–3602, 1998.
Emery et al., "Osteoprotegerin is a receptor for the cytotoxic ligand Trail", *J. Biol. Chem.*, 273, pp. 14363–14367, 1998.

\* cited by examiner

*Primary Examiner*—David S. Romeo
(74) *Attorney, Agent, or Firm*—William T. Han; Ratner & Prestia; William T. King

(57) ABSTRACT

The present invention relates to tumor necrosis factor receptor (TNF-R) related polypeptides and their ligands, hereinafter referred to as TR1, TR2, TL2 and TL4. The invention relates to methods to identify agonists and antagonists of TR1, TR2, TL2 and TL4.

4 Claims, No Drawings

SEQUENCE LISTING

<160> NUMBER OF SEQ ID NOS: 9

<210> SEQ ID NO 1
<211> LENGTH: 401
<212> TYPE: PRT
<213> ORGANISM: HOMO SAPIENS

<400> SEQUENCE: 1

Met Asn Lys Leu Leu Cys Cys Ala Leu Val Phe Leu Asp Ile Ser Ile
1               5                   10                  15

Lys Trp Thr Thr Gln Glu Thr Phe Pro Pro Lys Tyr Leu His Tyr Asp
            20                  25                  30

Glu Glu Thr Ser His Gln Leu Leu Cys Asp Lys Cys Pro Pro Gly Thr
        35                  40                  45

Tyr Leu Lys Gln His Cys Thr Ala Lys Trp Lys Thr Val Cys Ala Pro
    50                  55                  60

-continued

```
Cys Pro Asp His Tyr Tyr Thr Asp Ser Trp His Thr Ser Asp Glu Cys
 65                  70                  75                  80

Leu Tyr Cys Ser Pro Val Cys Lys Glu Leu Gln Tyr Val Lys Gln Glu
                 85                  90                  95

Cys Asn Arg Thr His Asn Arg Val Cys Glu Cys Lys Glu Gly Arg Tyr
            100                 105                 110

Leu Glu Ile Glu Phe Cys Leu Lys His Arg Ser Cys Pro Pro Gly Phe
        115                 120                 125

Gly Val Val Gln Ala Gly Thr Pro Glu Arg Asn Thr Val Cys Lys Arg
    130                 135                 140

Cys Pro Asp Gly Phe Phe Ser Asn Glu Thr Ser Ser Lys Ala Pro Cys
145                 150                 155                 160

Arg Lys His Thr Asn Cys Ser Val Phe Gly Leu Leu Leu Thr Gln Lys
                165                 170                 175

Gly Asn Ala Thr His Asp Asn Ile Cys Ser Gly Asn Ser Glu Ser Thr
            180                 185                 190

Gln Lys Cys Gly Ile Asp Val Thr Leu Cys Glu Glu Ala Phe Phe Arg
        195                 200                 205

Phe Ala Val Pro Thr Lys Phe Thr Pro Asn Trp Leu Ser Val Leu Val
    210                 215                 220

Asp Asn Leu Pro Gly Thr Lys Val Asn Ala Glu Ser Val Glu Arg Ile
225                 230                 235                 240

Lys Arg Gln His Ser Ser Gln Glu Gln Thr Phe Gln Leu Leu Lys Leu
                245                 250                 255

Trp Lys His Gln Asn Lys Asp Gln Asp Ile Val Lys Lys Ile Ile Gln
            260                 265                 270

Asp Ile Asp Leu Cys Glu Asn Ser Val Gln Arg His Ile Gly His Ala
        275                 280                 285

Asn Leu Thr Phe Glu Gln Leu Arg Ser Leu Met Glu Ser Leu Pro Gly
    290                 295                 300

Lys Lys Val Gly Ala Glu Asp Ile Glu Lys Thr Ile Lys Ala Cys Lys
305                 310                 315                 320

Pro Ser Asp Gln Ile Leu Lys Leu Leu Ser Leu Trp Arg Ile Lys Asn
                325                 330                 335

Gly Asp Gln Asp Thr Leu Lys Gly Leu Met His Ala Leu Lys His Ser
            340                 345                 350

Lys Thr Tyr His Phe Pro Lys Thr Val Thr Gln Ser Leu Lys Lys Thr
        355                 360                 365

Ile Arg Phe Leu His Ser Phe Thr Met Tyr Lys Leu Tyr Gln Lys Leu
    370                 375                 380

Phe Leu Glu Met Ile Gly Asn Gln Val Gln Ser Val Lys Ile Ser Cys
385                 390                 395                 400

Leu
```

<210> SEQ ID NO 2
<211> LENGTH: 283
<212> TYPE: PRT
<213> ORGANISM: HOMO SAPIENS

<400> SEQUENCE: 2

```
Met Glu Pro Pro Gly Asp Trp Gly Pro Pro Trp Arg Ser Thr Pro
  1               5                  10                  15

Arg Thr Asp Val Leu Arg Leu Val Leu Tyr Leu Thr Phe Leu Gly Ala
                 20                  25                  30
```

-continued

Pro Cys Tyr Ala Pro Ala Leu Pro Phe Cys Lys Glu Asp Glu Tyr Pro
                35                  40                  45

Val Gly Ser Glu Cys Cys Pro Lys Cys Ser Pro Gly Tyr Arg Val Lys
 50                  55                  60

Glu Ala Cys Gly Glu Leu Thr Gly Thr Val Cys Glu Pro Cys Pro Pro
 65                  70                  75                  80

Gly Thr Tyr Ile Ala His Leu Asn Gly Leu Ser Lys Cys Leu Gln Cys
                 85                  90                  95

Gln Met Cys Asp Pro Ala Met Gly Leu Arg Ala Ser Arg Asn Cys Ser
                100                 105                 110

Arg Thr Glu Asn Ala Val Cys Gly Cys Ser Pro Gly His Phe Cys Ile
            115                 120                 125

Val Gln Asp Gly Asp His Cys Ala Ala Cys Arg Ala Tyr Ala Thr Ser
    130                 135                 140

Ser Pro Gly Gln Arg Val Gln Lys Gly Gly Thr Glu Ser Gln Asp Thr
145                 150                 155                 160

Leu Cys Gln Asn Cys Pro Pro Gly Thr Phe Ser Pro Asn Gly Thr Leu
                165                 170                 175

Glu Glu Cys Gln His Gln Thr Lys Cys Ser Trp Leu Val Thr Lys Ala
                180                 185                 190

Gly Ala Gly Thr Ser Ser Ser His Trp Val Trp Trp Phe Leu Ser Gly
            195                 200                 205

Ser Leu Val Ile Val Ile Val Cys Ser Thr Val Gly Leu Ile Ile Cys
    210                 215                 220

Val Lys Arg Arg Lys Pro Arg Gly Asp Val Val Lys Val Ile Val Ser
225                 230                 235                 240

Val Gln Arg Lys Arg Gln Glu Ala Glu Gly Glu Ala Thr Val Ile Glu
                245                 250                 255

Ala Leu Gln Ala Pro Pro Asp Val Thr Thr Val Ala Val Glu Glu Thr
                260                 265                 270

Ile Pro Ser Phe Thr Gly Arg Ser Pro Asn His
            275                 280

<210> SEQ ID NO 3
<211> LENGTH: 279
<212> TYPE: PRT
<213> ORGANISM: HOMO SAPIENS

<400> SEQUENCE: 3

Met Met Glu Val Gln Gly Gly Pro Ser Leu Gly Gln Thr Cys Val Leu
  1               5                  10                  15

Ile Val Ile Phe Thr Val Leu Leu Gln Ser Leu Cys Val Ala Val Thr
                 20                  25                  30

Tyr Val Tyr Phe Thr Asn Glu Leu Lys Gln Met Gln Asp Lys Tyr Ser
                35                  40                  45

Lys Ser Gly Ile Ala Cys Phe Leu Lys Glu Asp Asp Ser Tyr Trp Asp
 50                  55                  60

Pro Asn Asp Glu Glu Ser Met Asn Ser Pro Cys Trp Gln Val Lys Trp
 65                  70                  75                  80

Gln Leu Arg Gln Leu Val Arg Lys Met Ile Leu Arg Thr Ser Glu Glu
                 85                  90                  95

Thr Ile Ser Thr Val Gln Glu Lys Gln Gln Asn Ile Ser Pro Leu Val
                100                 105                 110

Arg Glu Arg Gly Pro Gln Arg Val Ala Ala His Ile Thr Gly Thr Arg
            115                 120                 125

-continued

```
Gly Arg Ser Asn Thr Leu Ser Ser Pro Asn Ser Lys Asn Glu Lys Ala
        130                 135                 140
Leu Gly Arg Lys Ile Asn Ser Trp Glu Ser Ser Arg Ser Gly His Ser
145                 150                 155                 160
Phe Leu Ser Asn Leu His Leu Arg Asn Gly Glu Leu Val Ile His Glu
                165                 170                 175
Lys Gly Phe Tyr Tyr Ile Tyr Ser Gln Thr Tyr Phe Arg Phe Gln Glu
            180                 185                 190
Glu Ile Lys Glu Asn Thr Lys Asn Asp Lys Gln Met Val Gln Tyr Ile
        195                 200                 205
Tyr Lys Tyr Thr Ser Tyr Pro Asp Pro Ile Leu Leu Met Lys Ser Ala
    210                 215                 220
Arg Asn Ser Cys Trp Ser Lys Asp Ala Glu Tyr Gly Leu Tyr Ser Ile
225                 230                 235                 240
Tyr Gln Gly Gly Ile Phe Glu Leu Lys Glu Asn Asp Arg Ile Phe Val
                245                 250                 255
Ser Val Thr Asn Glu His Leu Ile Asp Met Asp His Glu Ala Ser Phe
            260                 265                 270
Phe Gly Ala Phe Leu Val Gly
        275

<210> SEQ ID NO 4
<211> LENGTH: 240
<212> TYPE: PRT
<213> ORGANISM: HOMO SAPIENS

<400> SEQUENCE: 4

Met Glu Glu Ser Val Val Arg Pro Ser Val Phe Val Val Asp Gly Gln
1               5                   10                  15
Thr Asp Ile Pro Phe Thr Arg Leu Gly Arg Ser His Arg Arg Gln Ser
            20                  25                  30
Cys Ser Val Ala Arg Val Gly Leu Gly Leu Leu Leu Leu Leu Met Gly
        35                  40                  45
Ala Gly Leu Ala Val Gln Gly Trp Phe Leu Leu Gln Leu His Trp Arg
    50                  55                  60
Leu Gly Glu Met Val Thr Arg Leu Pro Asp Gly Pro Ala Gly Ser Trp
65                  70                  75                  80
Glu Gln Leu Ile Gln Glu Arg Arg Ser His Glu Val Asn Pro Ala Ala
                85                  90                  95
His Leu Thr Gly Ala Asn Ser Ser Leu Thr Gly Ser Gly Gly Pro Leu
            100                 105                 110
Leu Trp Glu Thr Gln Leu Gly Leu Ala Phe Leu Arg Gly Leu Ser Tyr
        115                 120                 125
His Asp Gly Ala Leu Val Val Thr Lys Ala Gly Tyr Tyr Tyr Ile Tyr
    130                 135                 140
Ser Lys Val Gln Leu Gly Gly Val Gly Cys Pro Leu Gly Leu Ala Ser
145                 150                 155                 160
Thr Ile Thr His Gly Leu Tyr Lys Arg Thr Pro Arg Tyr Pro Glu Glu
                165                 170                 175
Leu Glu Leu Leu Val Ser Gln Gln Ser Pro Cys Gly Arg Ala Thr Ser
            180                 185                 190
Ser Ser Arg Val Trp Trp Asp Ser Ser Phe Leu Gly Gly Val Val His
        195                 200                 205
Leu Glu Ala Gly Glu Lys Val Val Val Arg Val Leu Asp Glu Arg Leu
    210                 215                 220
```

Val Arg Leu Arg Asp Gly Thr Arg Ser Tyr Phe Gly Ala Phe Met Val
225                 230                 235                 240

<210> SEQ ID NO 5
<211> LENGTH: 810
<212> TYPE: DNA
<213> ORGANISM: HOMO SAPIENS

<400> SEQUENCE: 5

| | | | | | |
|---|---|---|---|---|---|
| cccacgcgtc | cgcccacgcg | tccgctgagg | ttgaaggacc | caggcgtgtc | agccctgctc | 60 |
| cagacacctt | gggcatggag | gagagtgtcg | tacggccctc | agtgtttgtg | gtggatggac | 120 |
| agaccgacat | cccattcacg | aggctgggac | gaagccaccg | agacagtcg | tgcagtgtgg | 180 |
| cccgggtggg | tctgggtctc | ttgctgttgc | tgatggggggc | tgggctggcc | gtccaaggct | 240 |
| ggttcctcct | gcagctgcac | tggcgtctag | gagagatggt | cacccgcctg | cctgacggac | 300 |
| ctgcaggctc | ctgggagcag | ctgatacaag | agcgaaggtc | tcacgaggtc | aacccagcag | 360 |
| cgcatctcac | agggccaac | tccagcttga | ccggcagcgg | ggggccgctg | ttatgggaga | 420 |
| ctcagctggg | cctggccttc | ctgaggggcc | tcagctacca | cgatgggggcc | cttgtggtca | 480 |
| ccaaagctgg | ctactactac | atctactcca | aggtgcagct | gggcggtgtg | ggctgcccgc | 540 |
| tgggcctggc | cagcaccatc | acccacggcc | tctacaagcg | cacacccgc | taccccgagg | 600 |
| agctggagct | gttggtcagc | cagcagtcac | cctgcggacg | ggccaccagc | agctcccggg | 660 |
| tctggtggga | cagcagcttc | ctgggtggtg | tggtacacct | ggaggctggg | gagaaagtgg | 720 |
| tcgtccgtgt | gctggatgaa | cgcctggttc | gactgcgtga | tggtacccgg | tcttacttcg | 780 |
| gggctttcat | ggtgtgaagg | aaggagcgtg | | | | 810 |

<210> SEQ ID NO 6
<211> LENGTH: 8
<212> TYPE: PRT
<213> ORGANISM: HOMO SAPIENS

<400> SEQUENCE: 6

Arg Ser Ile Glu Gly Arg Gly Thr
1               5

<210> SEQ ID NO 7
<211> LENGTH: 6
<212> TYPE: PRT
<213> ORGANISM: HOMO SAPIENS

<400> SEQUENCE: 7

Ser Asp Asp Asp Asp Lys
1               5

<210> SEQ ID NO 8
<211> LENGTH: 8
<212> TYPE: PRT
<213> ORGANISM: HOMO SAPIENS

<400> SEQUENCE: 8

Arg Ser Ile Glu Gly Arg Gly Thr
1               5

<210> SEQ ID NO 9
<211> LENGTH: 6
<212> TYPE: PRT
<213> ORGANISM: HOMO SAPIENS

```
<400> SEQUENCE: 9

Ser Asp Asp Asp Asp Lys
1               5
```

METHOD OF IDENTIFYING AGONIST AND ANTAGONISTS FOR TUMOR NECROSIS RELATED RECEPTORS TR1 AND TR2

This application claims benefit of provisional applications U.S. No. 60/055,513, filed Aug. 13, 1997; No. 60/056,980 filed Aug. 26, 1997; and No. 60/057,550 filed Aug. 29, 1997. All three applications are incoiporated by reference herein.

FIELD OF INVENTION

The present invention relates to tumor necrosis factor receptor (TNF-R) related polypeptides (proteins) and their ligands, hereinafter referred to as TR1, TR2, TL2 and TL4. The invention also relates to inhibiting or activating the action of such polypeptides using agonists or antagonists by the screening methods described herein.

BACKGROUND OF THE INVENTION

Many biological actions are a response to certain stimuli and natural biological processes, and are controlled by factors, such as cytokines. These cytokines act through target cell receptors by engaging the receptor and producing an intracellular response.

For example, tumor necrosis factors (TNF) alpha and beta are cytokines which act through TNF receptors to regulate numerous biological processes, including protection against infection and induction of shock and inflammatory disease. The TNF molecules belong to the "TNF-ligand" superfamily, and act together with their receptors or counter-ligands, the "TNF-receptor" superfamily. So far, ten members of the TNF ligand superfamily have been identified and thirteen members of the TNF-receptor superfamily have been characterized.

Among the ligands there are included TNF-a, lymphotoxin-a (LT-a, also known as TNF-b), LT-b (found in complex heterotrimer LT-a2-b), FasL, CD40L, CD27L, CD30L, 4-1BBL, OX40L and TRAIL ((Wiley et al.Immunity 3: 673–682 (1995)) All but one of these (LTa) are expressed as type II membrane proteins. The superfamily of TNF receptors includes the p55TNF receptor, p75TNF receptor, TNF receptor-related protein, FAS antigen or APO-1, CD40, CD27, CD30, 4-1BB, OX40, low affinity p75, NGF-receptor(Meager, A., Biologicals, 22:291–295 (1994)).

Many members of the TNF-ligand superfamily are expressed by activated T-cells, implying that they are necessary for T-cell interactions with other cell types which underlie cell ontogeny and functions. (Meager, A., supra).

Considerable insight into the essential functions of several members of the TNF receptor family has been gained from the identification and creation of mutants that abolish the expression of these proteins. For example, naturally occurring mutations in the FAS antigen and its ligand cause lymphoproliferative disease (Watanabe-Fukunaga, R., et al., Nature 356:314 (1992)), perhaps reflecting a failure of programmed cell death. Mutations of the CD40 ligand cause an X-linked immunodeficiency state characterized by high levels of immunoglubulin M and low levels of immunoglobulin G in plasma, indicating faulty T-cell-dependent B-cell activation (Allen, R. C. et al., Science 259:990 (1993)). Targeted mutations of the low affinity nerve growth factor receptor cause a disorder characterized by faulty sensory innovation of peripheral structures (Lee, K. F. et al, Cell 69:737 (1992)).

TNF and LT-a are capable of binding to two TNF receptors (the 55- and 75-kd TNF receptors). A large number of biological effects elicited by TNF and LT-a, acting through their receptors, include hemorrhagic necrosis of transplanted tumors, cytotoxicity, a role in endotoxic shock, inflammation, immunoregulation, proliferation and antiviral responses, as well as protection against the deleterious effects of ionizing radiation. TNF and LT-a are involved in the pathogenesis of a wide range of diseases, including endotoxic shock, cerebral malaria, tumors, autoimmuine disease, AIDS and graft-host rejection (Beutler, B. and Von Huffel, C., Science 264:667–668 (1994)). Mutations in the p55 Receptor cause increased susceptibility to microbial infection.

Moreover, an about 80 amino acid domain near the C-terminus of TNFR1 (P55) and Fas was reported as the "death domain," which is responsible for transducing signals for programmed cell death (Tartaglia et al., Cell 74:845 (1993)). Other regions of the TNF receptor intracellular domain are responsible for the activation of transcription through NF-kB (Cheng and Baltimore Genes and Development 10: 963–973 (1996)). More recent evidence has suggested that receptors may induce signals in cells expressing membrane bound TNF family ligand in a process known as "reverse signaling" (Wiley et al., J. Immunol. 157:3635–3639.

The effects of TNF family ligands and TNF family receptors are varied and influence numerous functions, both normal and abnormal, in the biological processes of the mammalian system. There is a clear need, therefore, for identification and characterization of such receptors and ligands that influence biological activity, both normally and in disease states. In particular, there is a need to isolate and characterize novel members of the TNF receptor family.

This indicates that these Tumor necrosis factor receptors (TNF-R) have an established, proven history as therapeutic targets. Clearly there is a need for identification and characterization of further members of Tumor necrosis factor receptor (TNF-R) family which can play a role in preventing, ameliorating or correcting dysfunctions or diseases, including, but not limited to, chronic and acute inflammation, arthritis, septicemia, autoimmune diseases (eg inflammatory bowel disease, psoriasis), transplant rejection, graft vs. host disease, infection, stroke, ischemia, acute respiratory disease syndrome, restenosis, brain injury, AIDS, Bone diseases, cancer (eg lymphoproliferative disorders), atheroschlerosis, and Alzheimers disease.

SUMMARY OF THE INVENTION

The present invention relates to tumor necrosis factor receptor (TNF-R) related polypeptides and their ligands, hereinafter referred to as TR1, TR2, TL2 and TL4. The invention also relates to methods to identify agonists and antagonists of TR1, TR2, TL2 and TL4. The agonists and antagonists thus identified can be used to treat chronic and acute inflammation, arthritis, septicemia, autoimmune diseases (eg inflammatory bowel disease, psoriasis), transplant rejection, graft vs. host disease, infection, stroke, ischemia, acute respiratory disease syndrome, restenosis, brain injury, AIDS, bone diseases, cancer (eg lymphoproliferative disorders), atheroschlerosis, and Alzheimers disease, among others, caused by imbalance of TR1, TR2, TL2 or TL4.

DESCRIPTION OF THE INVENTION

"TR1 or TR1 polypeptide or TR1 protein" refers, among others, generally to a polypeptide having the amino acid sequence set forth in SEQ ID NO:1 as well as polypeptides comprising the amino acid sequence of SEQ ID NO: 1; and polypeptides comprising the amino acid sequence which have at least 70% identity to that of SEQ ID NO:1 over its entire length. Furthermore, TR1 also refers to a polypeptide which comprises a sequence which has 70% identity to a fragment of SEQ ID NO: 1. "TR1 or TR1 polypeptide or TR1 protein" also includes derivatives, such as fusion proteins, of the above polypeptides, and some of these derivatives are further illustrated below.

"TR2 or TR2 polypeptide or TR2 protein" refers, among others, generally to a polypeptide having the amino acid sequence set forth in SEQ ID NO:2 as well as polypeptides comprising the amino acid sequence of SEQ ID NO: 2; and polypeptides comprising the amino acid sequence which have at least 70% identity to that of SEQ ID NO:2 over its entire length. Furthermore, TR2 also refers to a polypeptide which comprises a sequence which has 70% identity to a fragment of SEQ ID NO: 2. "TR2 or TR2 polypeptide or TR2 protein" also includes derivatives, such as fusion proteins, of the above polypeptides, and some of these derivatives are further illustrated below.

"TL2 or TL2 polypeptide or TL2 protein" refers, among others, generally to a polypeptide having the amino acid sequence set forth in SEQ ID NO:3 as well as polypeptides comprising the amino acid sequence of SEQ ID NO: 3; and polypeptides comprising the amino acid sequence which have at least 70% identity to that of SEQ ID NO:3 over its entire length. Furthermore, TL2 also refers to a polypeptide which comprises a sequence which has 70% identity to a fragment of SEQ ID NO: 3. "TL2 or TL2 polypeptide or TL2 protein" also includes derivatives, such as fusion proteins, of the above polypeptides, and some of these derivatives are further illustrated below.

"TL4 or TL4 polypeptide or TL4 protein" refers, among others, generally to a polypeptide having the amino acid sequence set forth in SEQ ID NO:4 as well as polypeptides comprising the amino acid sequence of SEQ ID NO: 4; and polypeptides comprising the amino acid sequence which have at least 70% identity to that of SEQ ID NO:4 over its entire length. Furthermore, TL4 also refers to a polypeptide which comprises a sequence which has 70% identity to a fragment of SEQ ID NO: 4. "TL4 or TL4 polypeptide or TL4 protein" also includes derivatives, such as fusion proteins, of above polypeptides, and some of these derivatives are further illustrated below.

cDNA encoding polypeptide of SEQ ID NO:4 is contained in SEQ ID NO:5.

"Polypeptide" refers to any peptide or protein comprising two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than the 20 gene-encoded amino acids. "Polypeptides" include amino acid sequences modified either by natural processes, such as posttranslational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched as a result of ubiquitination, and they may be cyclic, with or without branching. Cyclic, branched and branched cyclic polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. See, for instance, PROTEINS—STRUCTURE AND MOLECULAR PROPERTIES, 2nd Ed., T. E. Creighton, W. H. Freeman and Company, New York, 1993 and Wold, F., Posttranslational Protein Modifications: Perspectives and Prospects, pgs. 1–12 in POSTTRANSLATIONAL COVALENT MODIFICATION OF PROTEINS, B. C. Johnson, Ed., Academic Press, New York, 1983; Seifter et al., "Analysis for protein modifications and nonprotein cofactors", Meth Enzymol (1990) 182:626–646 and Rattan et al., "Protein Synthesis: Posttranslational Modifications and Aging", Ann NY Acad Sci (1992) 663:48–62.

"Identity" is a measure of the identity of nucleotide sequences or amino acid sequences. In general, the sequences are aligned so that the highest order match is obtained. "Identity" per se has an art-recognized meaning and can be calculated using published techniques. See, e.g.: (COMPUTATIONAL MOLECULAR BIOLOGY, Lesk, A. M., ed., Oxford University Press, New York, 1988; BIOCOMPUTING: INFORMATICS AND GENOME PROJECTS, Smith, D. W., ed., Academic Press, New York, 1993; COMPUTER ANALYSIS OF SEQUENCE DATA, PART I, Griffin, A. M., and Griffin, H. G., eds., Humana Press, New Jersey, 1994; SEQUENCE ANALYSIS IN MOLECULAR BIOLOGY, von Heinje, G., Academic Press, 1987; and SEQUENCE ANALYSIS PRIMER, Gribskov, M. and Devereux, J., eds., M Stockton Press, New York, 1991). While there exist a number of methods to measure identity between two polynucleotide or polypeptide sequences, the term "identity" is well known to skilled artisans (Carillo, H., and Lipton, D., SIAM J Applied Math (1988) 48:1073). Methods commonly employed to determine identity or similarity between two sequences include, but are not limited to, those disclosed in Guide to Huge Computers, Martin J. Bishop, ed., Academic Press, San Diego, 1994, and Carillo, H., and Lipton, D., SIAM J Applied Math (1988) 48:1073. Methods to determine identity and similarity are codified in computer programs. Preferred computer program methods to determine identity and similarity between two sequences include, but are not limited to, GCG program package (Devereux, J., et al., Nucleic Acids Research (1984) 12(1):387), BLASTP, BLASTN, FASTA (Atschul, S. F. et al., J Molec Biol (1990) 215:403).

As an illustration, by a polypeptide having an amino acid sequence having at least, for example, 70% "identity" to a reference amino acid sequence of SEQ ID NO:2 is intended that the amino acid sequence of the polypeptide is identical to the reference sequence except that the polypeptide sequence may include up to thirty amino acid alterations per each 100 amino acids of the reference amino acid of SEQ ID NO: 2. In other words, to obtain a polypeptide having an amino acid sequence at least 70% identical to a reference amino acid sequence, up to 30% of the amino acid residues in the reference sequence may be deleted or substituted with another amino acid, or a number of amino acids up to 30% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

We have now discovered that TL2 of SEQ ID NO: 3 (otherwise known as TRAIL or Apo-2L, (Wiley S R, et al., *Immunity* (6):673–682 (1995); Pitt et al., J. Biol. Chem. 271: 12687–12690 (1996)) is a ligand of TR1 of SEQ ID NO:1 (otherwise known as osteoprotegerin (OPG), W. S. Simonet, et al., *Cell*, Vol 89, pp 309–319, 1997). Further, we also discovered that TL4 of SEQ ID NO: 4 is a ligand of TR2 of SEQ ID NO: 2 (described by R. I. Montgomery et al., *Cell*, Vol 87, pp427–436, 1996; Kwon et al., J. Biol. Chem. 272: 14272–14276 (1997); Hsu et al., J. Biol. Chem. 272:13471–13474 (1997))). Thus, the TR1 and TR2 polypeptides of the present invention, and their respective ligands, TL2 and TL4, can be employed in a screening process for compounds which bind to the receptors, or to their ligands, and which activate (agonists) or inhibit activation of (antagonists) TR1 and TR2 receptor polypeptides of the present invention, or their respective ligands TL2 and TL4. Thus, polypeptides of the invention may be used to assess the binding of small molecule substrates, receptors and ligands in, for example, cells, cell-free preparations, chemical libraries, and natural product mixtures. These substrates, receptors and ligands may be natural substrates and ligands, or may be structural or functional mimetics. See Coligan et al., *Current Protocols in Immunology* 1(2):Chapter 5 (1991).

TR1, TR2, TL2 and TL4 polypeptides are responsible for many biological functions, including many pathologies. Accordingly, it is desirous to find compounds and drugs which stimulate TR1, TR2, TL2 or TL4 on the one hand, and which can inhibit the function of TR1, TR2, TL2 or TL4 or remove TR1, TR2, TL2 or TL4 expressing cells on the other hand (also defined as antagonists). Antagonists for TR1, TR2, TL2, and TL4 (including agents which remove TR1, TR2, TL2 or TL4 expressing cells) may be employed for a variety of therapeutic and prophylactic purposes for such conditions as chronic and acute inflammation, arthritis, septicemia, autoimmune diseases (e.g. inflammatory bowel disease, psoriasis), transplant rejection, graft vs. host disease, infection, stroke, ischemia, acute respiratory disease syndrome, restenosis, brain injury, AIDS, Bone diseases, cancer (e.g. lymphoproliferative disorders), atheroschlerosis, and Alzheimers disease. Agonists can be employed for therapeutic and prophylactic purposes for such conditions responsive to activation of T cells and other components of the immune system, such as for treatment of cancer and AIDS. However, agonists can also be employed for inappropriate stimulation of T cells and other components of the immune system which leads to down modulation of immune activity with therapeutic or prophylactic application for conditions such, as chronic and acute inflammation, arthritis, septicemia, autoimmune diseases (e.g. inflammatory bowel disease, psoriasis), transplant rejection, graft vs. host disease, infection, stroke, ischemia, acute respiratory disease syndrome, restenosis, brain injury, bone diseases, atheroschlerosis, and Alzheimers disease.

Antagonists may be identified using assays to detect compounds which inhibit binding of TL2 to TR1 (or TL4 to TR2) in either cell-free or cell based assays. Suitable cell-free assays may be readily determined by one of skill in the art. For example, an ELISA format may be used in which purified TR1 (or TR2), or a purified derivative of TR1 (or TR2), such as a fusion protein, containing the extracellular domain of TR1 (or TR2), is immobilized on a suitable surface, either directly or indirectly (e.g., via an antibody to TR1 (or TR2) or to the fused epitope or protein domain) and candidate compounds are identified by their ability to block binding of purified soluble, extracellular domain of TL2 to TR1 (or soluble, extracellular domain of TL4 to TR2). The binding of TL2 to TR1 (or TL4 to TR2) could be detected by using a label directly or indirectly associated with TL2 (or TL4). Suitable detection systems include the streptavidin horseradish peroxidase conjugate, or direct conjugation by a tag, e.g., fluorescein. Conversely, purified, soluble TL2 (or TL4) may be immobilized on a suitable surface, and candidate compounds identified by their ability to block binding of purified TR1 to TL2 (or TR2 to TL4). The binding of TR1 to TL2 (or TR2 to TL4) could be detected by using a label directly or indirectly associated with TR1 (or TR2). Many other assay formats are possible that use the TR1 (or TR2) protein and its ligands.

Suitable cell based assays may be readily determined by one of skill in the art. In general, such screening procedures involve producing appropriate cells which express the receptor polypeptides (or ligands thereof) of the present invention on the surface thereof. Such cells include cells from mammals, yeast, Drosophila or E. coli. Cells expressing the receptor, such as TR1 or TR2, (or cell membrane containing the expressed receptor) are then contacted with a ligand, such as TL2 or TL4, or test compound to observe binding, or stimulation or inhibition of a functional response. The assays may simply test binding of a candidate compound wherein adherence to the cells bearing the receptor is detected by means of a label directly or indirectly associated with the candidate compound or in an assay involving competition with a labeled competitor, such as the ligands TL2 or TL4. Alternatively, cells expressing the ligand, such as TL2 or TL4, (or cell membrane containing the expressed ligand) are then contacted with a receptor, such as TR1 or TR2, or test compound to observe binding, or stimulation or inhibition of a functional response. Similarly, the assays may simply test binding of a candidate compound wherein adherence to the cells bearing the ligand is detected by means of a label directly or indirectly associated with the candidate compound or in an assay involving competition with a labeled competitor, such as the receptors TR1 and TR2. Further, these assays may test whether the candidate compound results in a signal generated by activation of the receptor (e.g TR1 or TR2) or its respective ligand (e.g. TL2 or TL4) using detection systems appropriate to the cells bearing the receptor or its ligand and fusion proteins thereof at their surfaces. Typical fusion partners include fusing the extracellular domain of the receptor or ligand with the intracellular tyrosine kinase domain of a second receptor. Inhibitors of activation are generally assayed in the presence of an agonist, such as the ligand TL2 or TL4 for cells expressing TR1 and TR2 receptors or receptor fusions respectively, or the receptor TR1 and TR2 with cells expressing TL2 and TL4 ligands and ligand fusions, and the effect on activation by the agonist by the presence of the candidate compound is observed. Standard methods for conducting such screening assays are well understood in the art.

Examples of potential TR1 or TR2 antagonists include antibodies or, in some cases, proteins which are closely related to the ligand of the TR1 or TR2, e.g., a fragment of the respective ligand TL2 or TL4, or small molecules which bind to the receptor, or its ligand, but do not elicit a response, so that the activity of the receptor is prevented. Examples of potential TR1 or TR2 agonists include antibodies that bind to TR1 or TR2, its respective ligand, such as TL2 or TL4, or derivatives thereof, and small molecules that bind to TR1 or TR2. These agonists will elicit a response mimicking all or part of the response induced by contacting the native ligand.

Since receptors may also invoke signals in cells expressing the membrane TL2 and TL4, these screens may also yield agonists which mimic the agonist activity of TR1 with membrane TL2 and TR2 with membrane TL4. Examples of potential TL2 or TL4 agonists include antibodies that bind to TL2 or TL4, its respective receptor, such as TR1 or TR2, or derivatives thereof, and small molecules that bind to TL2 or TL4. These agonists will elicit a response mimicking all or part of the response induced by contacting the native ligand. Alternatively, TR1 or TR2 may be expressed as a soluble protein, including versions which fuse all or part of TR1 or TR2 with a convenient partner peptide for which detection reagents are available, eg TR1-IgG or TR2-IgG fusions, and used in a solid state or solution phase binding assay. For example, the soluble TR1 or TR2 can be used to detect agonist or antagonist binding directly through changes that can be detected experimentally, eg surface plasmon resonance, nuclear magnetic resonance spectrometry, sedimentation, calorimetry. The soluble TR1 or TR2 can be used to detect agonist or antagonist binding indirectly by looking for competition of the candidate agonist or antagonist with a ligand, such as TL2 or TL4, whose binding can be detected. Ligand detection methods include antibody recognition, modification of the ligand via radioactive labeling, chemical modification (eg biotinylation), fusion to an epitope tag. Methods include ELISA based assays, immunoprecipitation and scintillation proximity.

Assays similar to those described above using soluble or membrane bound TR1 or TR2 may also be used to identify and purify additional natural ligand(s) of TR1 or TR2. These ligands may be agonists or antagonists of the receptor.

Thus the invention relates to:

I. A method for identifying agonists or antagonists to TR1 or TR2 comprising:
   (a) contacting a candidate compound with TR1 or TR2 in the presence of labeled or unlabeled ligand TL2 or TL4 respectively; and
   (b) assessing the ability of said candidate compound to compete with TL2 or TL4 binding to TR1 or TR2 respectively;
II. The method of I in which TR1 or TR2 is on the surface of a host cell, on a cell membrane or on a solid support;
III. The method of II for identifying agonists which further includes determining whether the candidate compound affects a signal generated by TR1 or TR2 polypeptide at the surface of the cell, wherein a candidate compound which increases production of said signal is identified as an agonist;
IV. An agonist identified by the method of I, II or III;
V. The method of II for identifying antagonists which further includes determining whether the candidate compound affects a signal generated by TR1 or TR2 polypeptide at the surface of the cell, wherein a candidate compound which diminishes production of said signal is identified as an antagonist;
VI. An antagonist identified by the method of I, II or V;
VII. A method for identifying agonists or antagonists to TL2 or TL4 comprising:
   (a) contacting a candidate compound with TL2 or TL4 in the presence of labeled or unlabeled TR1 or TR2 respectively; and
   (b) assessing the ability of said candidate compound to compete with TR1 or TR2 binding to TL2 or TL4 respectively;
VIII. The method of VII in which TL2 or TL4 is on the surface of a host cell, on a cell membrane or on a solid support;
IX. The method of VIII for identifying agonists to TL2 or TL4 which includes determining whether the candidate compound affects a signal generated by TL2 or TL4 polypeptide at the surface of the cell, wherein a candidate compound which increases production of said signal is identified as an agonist;
X. An agonist identified by the method of IX;
XI. The method of VIII for identifying antagonists which further includes determining whether the candidate compound affects a signal generated by TL2 or TL4 polypeptide at the surface of the cell, wherein a candidate compound which diminishes production of said signal is identified as an antagonist; and
XII. An antagonist identified by the method XI.

Thus in another aspect, the present invention relates to a screening kit for identifying agonists, antagonists, ligands, receptors, substrates, enzymes, etc. for TR1, TR2, TL2 or TL4 polypeptides; which comprises:
(a) a TR1, TR2, TL2 or TL4 polypeptide, preferably that of SEQ ID NO:1, 2, 3 or 4;
(b) a recombinant cell expressing a TR1, TR2, TL2 or TL4 polypeptide, preferably that of SEQ ID NO: 1, 2, 3or 4;
(c) a cell membrane expressing a TR1, TR2, TL2 or TL4 polypeptide; preferably that of SEQ ID NO: 1,2,3 or4; or
(d) antibody to a TR1, TR2, TL2 or TL4 polypeptide, preferably that of SEQ ID NO: 1, 2, 3 or 4. It will be appreciated that in any such kit, (a), (b), (c) or (d) may comprise a substantial component.

Prophylactic and Therapeutic Methods

This invention provides methods of treating an abnormal conditions related to both an excess of and insufficient amounts of TR1, TR2, TL2 or TL4 polypeptide activity.

If the activity of TR1, TR2, TL2 or TL4 polypeptide is in excess, several approaches are available. One approach comprises administering to a subject an inhibitor compound (antagonist) as hereinabove described along with a pharmaceutically acceptable carrier in an amount effective to inhibit activation by blocking binding of ligands to the TR1 or TR2 polypeptide, or by inhibiting a second signal, and thereby alleviating the abnormal condition.

In another approach, soluble forms of TR1 or TR2 polypeptides still capable of binding the ligand in competition with endogenous TR1 or TR2 polypeptide may be administered. Typical embodiments of such competitors comprise fragments of the TR1 or TR2 polypeptide.

For treating abnormal conditions related to an underexpression of TR1, TR2, TL2 or TL4 and its activity, several approaches are also available. One approach comprises administering to a subject a therapeutically effective amount of a compound which activates TR1, TR2, TL2 or TL4 polypeptide, i.e., an agonist as described above, in combination with a pharmaceutically acceptable carrier, to thereby alleviate the abnormal condition.

Formulation and Administration

Agonists and antagonist of TR1, TR2, TL2 or TL4 may be formulated in combination with a suitable pharmaceutical carrier. Such formulations comprise a therapeutically effective amount of the polypeptide or compound, and a pharmaceutically acceptable carrier or excipient. Such carriers include but are not limited to, saline, buffered saline, dextrose, water, glycerol, ethanol, and combinations thereof. Formulation should suit the mode of administration, and is well within the skill of the art. The invention further relates to pharmaceutical packs and kits comprising one or more containers filled with one or more of the ingredients of the aforementioned compositions of the invention.

Polypeptides and other compounds of the present invention may be employed alone or in conjunction with other compounds, such as therapeutic compounds.

Preferred forms of systemic administration of the pharmaceutical compositions include injection, typically by intravenous injection. Other injection routes, such as subcutaneous, intramuscular, or intraperitoneal, can be used. Alternative means for systemic administration include transmucosal and transdermal administration using penetrants such as bile salts or fusidic acids or other detergents. In addition, if properly formulated in enteric or encapsulated formulations, oral administration may also be possible. Administration of these compounds may also be topical and/or localized, in the form of salves, pastes, gels and the like.

The dosage range required depends on the choice of peptide or compound, the route of administration, the nature of the formulation, the nature of the subject's condition, and the judgment of the attending practitioner. Suitable dosages, however, are in the range of 0.1–100 µg/kg of subject. Wide variations in the needed dosage, however, are to be expected in view of the variety of compounds available and the differing efficiencies of various routes of administration. For example, oral administration would be expected to require higher dosages than administration by intravenous injection. Variations in these dosage levels can be adjusted using standard empirical routines for optimization, as is well understood in the art.

The examples below are carried out using standard techniques, which are well known and routine to those of skill in the art, except where otherwise described in detail. The examples illustrate, but do not limit the invention.

EXAMPLES

The expression and determination of receptor ligand pairings for TL2, TL4, TR1 and TR2 are described below. TL2 is also known as TRAIL (Wiley et al. Immunity 3: 673–682 (1995)) or Apo-2L (Pitti et al., J. Biol. Chem. 271:12687–12690 (1996)). TR1 is also known as osteoprotegerin Simonet et al., Cell 89:309–319 (1997). TR2 is also known as HVEM (Montgomery et al., Cell 87:427–436 (1996)).

Expression

TR1 and TR2 were expressed as fusion proteins in which the extracellular domain of either receptor was fused at its amino terminus with the hinge-CH2-CH3 region of human IgG1. The junction between the two protein domains was engineered to include the amino acid sequence for proteolytic cleavage by Factor Xa. When expressed in this form in mammalian cells, the TR fusion proteins (TR1Fc and TR2 Fc respectively) were secreted as dimeric proteins, and were purified by protein A sepharose. The non-fused soluble receptor was generated from the TR2 or TR1Fc fusion by incubation with bovine Factor Xa and was purified away from the Fc portion by repassage over protein A sepharose and pooling of the flow through.

TL2 and TL4 are both type II membrane proteins in which it is the C-terminus which is extracellular. These were expressed as secreted fusion proteins by engineering an expression DNA construct in which the DNA encoding a substantial part of the carboxyterminal region, which includes all of the residues homologous to mature TNF, was fused to an amino terminal epitope tag sequence, and an amino terminal hydrophobic signal sequence for secretion, detection and purification. When transfected into mammalian cells, these DNA constructs resulted in the secretion of soluble, epitope tagged fusion proteins (sTL2, sTL4 respectively). Specific details of the construction of each expression vector are given below.

TR2

The putative transmembrane domain of translated TR2 sequence was determined by hydrophobicity using the method of Goldman et al (1) for identifying nonpolar transbilayer helices. The region upstream of this transmembrane domain, encoding the putative leader peptide and extracellular domain, was chosen for the production of an Fc fusion protein. Primers were designed to PCR the corresponding coding region from the TR2 cDNA with the addition of a BglII site, a Factor Xa protease cleavage site and an Asp718I site at the 3' end. PCR with this primer pair (forward 35-mer 5' cag gaa ttc gca gcc atg gag cct cct gga gac tg 3' (SEQ ID NO: 6), and reverse primer 53-mer 5' cca tac cca ggt acc cct tcc ctc gat aga tct tgc ctt cgt cac cag cca gc 3' (SEQ ID NO: 7)) resulted in one band of the expected size. This was cloned into COSFclink to give the TR2Fclink plasmid. The PCR product was digested with EcoRI and Asp718I and ligated into the COSFclink plasmid (2, 3) to produce TR2Fclink. This vector encodes amino acids 1–192 of TR2, followed by the amino acids RSIEGRGT (SEQ ID NO:8) for Factor Xa cleavage, followed by residues 226–458 (end) of human IgG1. The IgG1 region also has a mutation of Cys230 to Ala (2).

COS cells were transiently transfected with TR2Fclink and the resulting supernatant was immunoprecipitated with protein A agarose. Western blot analysis of the immunoprecipitate using goat anti-human Fc antibodies revealed a strong band consistent with the expected size for glycosylated TR2Fc (greater than 47.5 kD).

CHO cells were transfected with TR2Fclink to produce stable cell lines. Five lines were chosen by dot blot analysis for expansion and were adapted to shake flasks. The line with the highest level of TR2Fc protein expression was chosen by Western blot analysis.

TR1

The sequence of TR1 did not show any transmembrane region by hydrophobicity plot (Goldman et al., see TR2 above). The entire coding region of TR1 minus the terminator codon was therefore used to produce an Fc fusion construct. The TR2 insert in TR2Fclink was replaced with TR1 as follows. The 3' end of TR1 was amplified from a TR1 cDNA using the following primers: 5' cgc ccc ttg ccc tga cca cta 3' (SEQ ID NO: 8) (upstream of HindIII site) and 5' gcc att tca gat ctt aag cag ctt att ttt act ga 3' (SEQ ID NO: 9) (replaces stop codon with BglII site). The PCR products were cloned into pCR2 (Invitrogen; pCR2TR1) and sequenced. TR2Fclink was digested with EcoRI BglII and calf intestinal phosphatase, then ligated with the EcoRI/HindIII fragment of TR1 cDNA and HindIII/BglII fragment of pCR2TR1 to form TR1Fclink.

Confirmation of TR1Fc expression in transiently transfected COS cells was determined and stable cell lines established as for TR2Fc.

TL2

The soluble form of TL2 was identical to that previously published (Wiley et al., Immunity 3:673–682 (1995)). Residues 95–281 of the full length TL2 (also known as TRAIL, Apo-2L) were fused to the tPA (tissue plasminogen activator) signal sequence and the FLAG epitope. The resulting DNA construct was transfected into COS and CHO cells, and TL2 was secreted into the supernatant. The protein (sTL2) was purified by passage over an affinity column containing the M2 anti-FLAG epitope antibody available commercially.

TL4

An expression vector was constructed which contained the tPA (tissue plasminogen activator) signal sequence, an 11 amino acid sequence derived from HIV-1 gp 120 glycoprotein, six histidines, the enterokinase proteolytic sequence SDDDDK (SEQ ID NO:8) followed by residues 85–240 of the coding region of TL4. This construct was transfected into COS and CHO cells and resulted in the secretion of a soluble form of TL4 (sTL4). The protein was purified by passage over a NiNTA column (available commercially) which binds to the polyhistidine sequence at the amino terminus of the fusion protein. Cleavage of the fusion protein with enterokinase yielded mature TL4.

Binding Studies

Surface plasmon resonance. Protein A was immobilized on to a research grade carboxymethyldextran chip (CM5) using amin coupling procedures described previously (4). Flow cell 1 was activated with NHS/EDC for 5 min. Protein A was injected a a concentration of 1 ug/ml in NaOAc buffer (10 mM, pH 5.0) until 1000 RUs of protein were coupled. Remaining activated groups were blocked with a 7 min injection of 1M ethanolamine. A control surface was created by repeating the coupling procedure in a flow cell2 without incorporating protein A. In a BIAcore 2000 biosensor (BIAcore Inc. Uppsala, Sweden) TR1Fc or TR2Fc were then injected at a flow rate of 100 ul/min followed by injection of TL2 or TL4, and the binding to receptor monitored by changes in surface plasmon resonance relative to the control chip. In these experiments, TR1Fc bound to TL2 but not TL4 and TR2Fc bound to TL4 but not TL2.

Receptor Precipitation

We examined the ability of TR1Fc and TR2Fc to precipitate TL2 or TL4 in solution followed by detection of the ligand in a western blot using antibodies against the fused epitope tag the ligands or the ligand itself. In a typical experiment, 2 ug of TR1Fc or TR2Fc receptor was incubated with 250 ng of purified TL2 or TL4 respectively in binding buffer (25 mM HEPES pH 7.2, 0.1% BSA, 0.01% TWEEN in RPMI 1640). After binding for four hours, receptor complexes were captured on protein A sepharose, centrifuged, washed with binding buffer, electrophoresed on 15% SDS PAGE and transferred for western blotting. TL4 was detected by antibodies to its epitope tag (a 1:5000 dilution of a mixture of murine monoclonal antibodies to the gp120 peptide epitope and the poyHis tail of both antibodies) and demonstrated to bind to TR2 but not TR1Fc or other TNFR related Fc fusion proteins. TL2 ws detected by a 1:5000 dilution of a rabbit polyclonal antiserum raised to TL2 expressed and purified from E. coli, and was found to bind to TR1Fc but not to TR2Fc or other TNFR related Fc fusion proteins. Specificity of binding was further confirmed by the ability of the soluble cleaved TR1 or TR2 to compete with the binding of TR1Fc to TL2 and TR2Fc to TL4 respectively.

The references cited in this EXAMPLES Section are as follows:

1. Engelman-D M; Steitz-T A; Goldman-A. Identifying nonpolar transbilayer helices in amino acid sequences of membrane proteins. Annu-Rev-Biophys-Biophys-Chem. 1986; 15: 321–53.
2. Johanson-K; Appelbaum-E; Doyle-M; Hensley-P; Zhao-B; Abdel-Meguid-S S; Young-P; Cook-R; Carr-S; Matico-R; et-al. Binding interactions of human interleukin 5 with its receptor alpha subunit. Large scale production, structural, and functional studies of Drosophila-expressed recombinant proteins. J-Biol-Chem. Apr. 21, 1995; 270 (16): 9459–71.
3. Kumar-S; Minnich-M D; Young-P R. ST2/T1 protein functionally binds to two secreted proteins from Balb/c 3T3 and human umbilical vein endothelial cells but does not bind interleukin 1. J-Biol-Chem. Nov. 17, 1995; 270(46): 27905–13.
4. Johnsson, B., Lofas, S. And Lindquist, G. (1991). Immobilization of proteins to a carboxymethyldextran-modified gold surface for biospecific interaction analysis in surface plasmon resonance sensors. Anal. Biochem. 198:268–277.

What is claimed is:

1. A method for assessing the ability of a candidate compound to compete with the binding of the polypeptide set forth in SEQ ID NO:4 to the polypeptide set forth in SEQ ID NO: 2 comprising:
   (a) contacting a candidate compound with the polypeptide set forth in SEQ ID NO: 2 in the presence of labeled or unlabeled polypeptide as set forth in SEQ ID NO: 4; and
   (b) assessing the ability of said candidate compound to compete with the binding of the polypeptide set forth in SEQ ID NO: 4 to the polypeptide set forth in SEQ ID NO: 2.

2. The method of claim 1 in which the polypeptide set forth in SEQ ID NO: 2 is on the surface of a host cell, on a cell membrane or on a solid support.

3. A method for assessing the ability of a candidate compound to compete with the binding of the polypeptide set forth in SEQ ID NO:2 to the polypeptide set forth in SEQ ID NO: 4 comprising:
   (a) contacting a candidate compound with the polypeptide set forth in SEQ ID NO: 4 in the presence of labeled or unlabeled the polypeptide set forth in SEQ ID NO: 2; and
   (b) assessing the ability of said candidate compound to compete with the binding of the polypeptide set forth in SEQ ID NO: 2 to the polypeptide set forth in SEQ ID NO: 4.

4. The method of claim 3 in which the polypeptide set forth in SEQ ID NO: 4 is on the surface of a host cell, on a cell membrane or on a solid support.

* * * * *